(12) United States Patent  (10) Patent No.: US 8,900,231 B2
Kreindel  (45) Date of Patent: Dec. 2, 2014

(54) METHOD AND SYSTEM FOR INVASIVE SKIN TREATMENT

(75) Inventor: Michael Kreindel, Haifa (IL)

(73) Assignee: Syneron Medical Ltd, Yokneam (IL)

( * ) Notice: Subject to any disclaimer, the term of this patent is extended or adjusted under 35 U.S.C. 154(b) by 641 days.

(21) Appl. No.: 12/702,647

(22) Filed: Feb. 9, 2010

(65) Prior Publication Data

US 2010/0185193 A1 Jul. 22, 2010

Related U.S. Application Data

(63) Continuation of application No. 10/931,271, filed on Sep. 1, 2004, now abandoned.

(51) Int. Cl.
  A61B 18/14 (2006.01)
  A61B 18/18 (2006.01)
  A61B 18/00 (2006.01)

(52) U.S. Cl.
  CPC ............. *A61B 18/18* (2013.01); *A61B 18/1477* (2013.01); *A61B 18/14* (2013.01); *A61B 2018/1467* (2013.01); *A61B 2018/1425* (2013.01); *A61B 2018/143* (2013.01); *A61B 2018/00452* (2013.01)
  USPC .............................................. 606/49; 606/41

(58) Field of Classification Search
  USPC ................... 606/32, 40, 41, 49; 607/101, 102
  See application file for complete search history.

(56) References Cited

U.S. PATENT DOCUMENTS

| | | | |
|---|---|---|---|
| 1,430,354 A | 9/1922 | Burdick | |
| 2,088,780 A | 8/1937 | Follese | |
| 2,183,726 A | 2/1939 | Sommer et al. | |
| 2,231,095 A | 2/1941 | Sommer et al. | |
| 2,727,132 A | 12/1955 | Hills | |
| 2,824,308 A | 2/1958 | Duncan | |
| 2,888,927 A | 6/1959 | Fozard | |
| 3,088,205 A | 5/1963 | Ellis | |
| D196,532 S | 10/1963 | Facci | |
| 4,016,886 A | 4/1977 | Doss et al. | |
| 4,174,713 A | 11/1979 | Mehl | |
| 4,182,329 A | 1/1980 | Smit et al. | |
| 4,185,632 A | 1/1980 | Shaw | |
| 4,200,104 A | 4/1980 | Harris | |
| 4,211,230 A | 7/1980 | Woltosz | |
| 4,228,931 A | 10/1980 | Ruscitti et al. | |
| 4,321,926 A | 3/1982 | Roge | |
| D269,294 S | 6/1983 | Rakocy et al. | |
| D271,015 S | 10/1983 | Geraets | |
| D271,199 S | 11/1983 | Geraets | |

(Continued)

FOREIGN PATENT DOCUMENTS

CN 1078383 A 11/1993
EP 0528055 A1 2/1993

(Continued)

*Primary Examiner* — Michael Peffley

(74) *Attorney, Agent, or Firm* — Smith Risley Tempel Santos LLC; Gregory Scott Smith

(57) ABSTRACT

A system and method for simultaneously heating a plurality of discrete skin volumes to a coagulation temperature. The system comprises an applicator containing an electrode having a plurality of spaced apart protruding conducting elements configured to contact the skin surface at a plurality of discrete locations. A controller applies a voltage to the electrode so as to simultaneously heat a plurality of skin volumes to a coagulation temperature when the applicator is applied to the skin surface.

12 Claims, 2 Drawing Sheets

(56) References Cited

U.S. PATENT DOCUMENTS

| | | |
|---|---|---|
| 4,444,190 A | 4/1984 | Mutzhas |
| D274,462 S | 6/1984 | Rakocy et al. |
| 4,532,924 A | 8/1985 | Auth et al. |
| 4,550,728 A | 11/1985 | Runyon et al. |
| 4,553,936 A | 11/1985 | Wang |
| 4,566,454 A | 1/1986 | Mehl et al. |
| 4,686,986 A | 8/1987 | Fenyo et al. |
| 4,753,958 A | 6/1988 | Weinstein et al. |
| 4,784,135 A | 11/1988 | Blum et al. |
| 4,844,063 A | 7/1989 | Clark |
| 4,867,682 A | 9/1989 | Hammesfahr et al. |
| 4,869,584 A | 9/1989 | Dion |
| 5,016,999 A | 5/1991 | Williams |
| 5,071,418 A | 12/1991 | Rosenbaum |
| 5,125,928 A | 6/1992 | Parins et al. |
| 5,169,384 A | 12/1992 | Bosniak et al. |
| 5,286,479 A | 2/1994 | Garlich et al. |
| 5,316,473 A | 5/1994 | Hare |
| 5,348,554 A | 9/1994 | Imran et al. |
| 5,353,798 A | 10/1994 | Sieben |
| 5,383,874 A | 1/1995 | Jackson et al. |
| 5,402,697 A | 4/1995 | Brooks |
| 5,406,340 A | 4/1995 | Hoff |
| 5,418,130 A | 5/1995 | Platz et al. |
| 5,449,378 A | 9/1995 | Schouenborg |
| 5,487,662 A | 1/1996 | Kipke et al. |
| 5,509,916 A | 4/1996 | Taylor |
| 5,520,684 A | 5/1996 | Imran |
| 5,521,392 A | 5/1996 | Kennedy et al. |
| 5,564,851 A | 10/1996 | Connely et al. |
| 5,582,476 A | 12/1996 | Hansen |
| 5,611,793 A | 3/1997 | Wilson et al. |
| 5,628,771 A | 5/1997 | Mizukawa et al. |
| 5,642,997 A | 7/1997 | Gregg et al. |
| 5,658,148 A | 8/1997 | Neuberger et al. |
| 5,674,267 A | 10/1997 | Mir et al. |
| 5,683,380 A | 11/1997 | Eckhouse et al. |
| 5,693,052 A | 12/1997 | Weaver |
| 5,698,866 A | 12/1997 | Doiron et al. |
| 5,704,935 A | 1/1998 | Pahl et al. |
| 5,707,403 A | 1/1998 | Grove et al. |
| 5,718,702 A | 2/1998 | Edwards |
| 5,722,411 A | 3/1998 | Suzuki et al. |
| 5,731,582 A | 3/1998 | West |
| 5,735,844 A | 4/1998 | Anderson et al. |
| 5,755,753 A | 5/1998 | Knowlton |
| 5,769,880 A | 6/1998 | Truckai et al. |
| 5,810,801 A | 9/1998 | Anderson et al. |
| 5,814,008 A | 9/1998 | Chen et al. |
| 5,824,023 A | 10/1998 | Anderson |
| 5,836,999 A | 11/1998 | Eckhouse et al. |
| 5,843,143 A | 12/1998 | Whitehurst |
| 5,846,252 A | 12/1998 | Mehl, Sr. |
| 5,868,744 A | 2/1999 | Willmen |
| 5,871,469 A | 2/1999 | Eggers et al. |
| 5,871,524 A | 2/1999 | Knowlton |
| 5,888,198 A | 3/1999 | Eggers et al. |
| 5,919,219 A | 7/1999 | Knowlton |
| 5,935,143 A | 8/1999 | Hood |
| 5,949,514 A | 9/1999 | Wargon |
| 5,954,710 A | 9/1999 | Paolini et al. |
| 5,961,543 A | 10/1999 | Waldmann |
| 5,984,915 A | 11/1999 | Loeb et al. |
| 5,993,180 A | 11/1999 | Westerhof et al. |
| 6,024,733 A | 2/2000 | Eggers et al. |
| 6,030,384 A | 2/2000 | Nezhat |
| 6,053,172 A | 4/2000 | Hovda et al. |
| 6,056,548 A | 5/2000 | Neuberger et al. |
| 6,063,108 A | 5/2000 | Salansky et al. |
| 6,066,134 A | 5/2000 | Eggers et al. |
| 6,080,127 A | 6/2000 | Li et al. |
| 6,080,391 A | 6/2000 | Tsuchiya et al. |
| 6,081,934 A | 7/2000 | Stefanovsky et al. |
| 6,107,326 A | 8/2000 | Jori |
| 6,132,701 A | 10/2000 | Perez et al. |
| 6,148,232 A | 11/2000 | Avrahami |
| 6,159,222 A | 12/2000 | Yiu |
| 6,186,960 B1 | 2/2001 | Tripp et al. |
| 6,187,001 B1 | 2/2001 | Azar et al. |
| 6,188,407 B1 | 2/2001 | Smith et al. |
| 6,190,609 B1 | 2/2001 | Chapman et al. |
| 6,191,110 B1 | 2/2001 | Jaynes et al. |
| 6,210,402 B1 | 4/2001 | Olsen et al. |
| 6,221,095 B1 | 4/2001 | Van Zuylen et al. |
| 6,228,078 B1 | 5/2001 | Eggers et al. |
| 6,231,571 B1 | 5/2001 | Ellman et al. |
| 6,231,593 B1 | 5/2001 | Meserol |
| 6,251,127 B1 | 6/2001 | Biel |
| 6,258,319 B1 | 7/2001 | Hearst et al. |
| 6,273,884 B1 | 8/2001 | Altshuler et al. |
| 6,277,116 B1 * | 8/2001 | Utely et al. ..................... 606/42 |
| 6,280,438 B1 | 8/2001 | Eckhouse et al. |
| 6,288,498 B1 | 9/2001 | Cheng |
| 6,308,413 B1 | 10/2001 | Westerhof et al. |
| 6,309,387 B1 | 10/2001 | Eggers et al. |
| 6,311,090 B1 | 10/2001 | Knowlton |
| 6,325,797 B1 | 12/2001 | Stewart et al. |
| 6,343,400 B1 | 2/2002 | Massholder et al. |
| 6,343,933 B1 | 2/2002 | Montgomery et al. |
| 6,352,535 B1 | 3/2002 | Lewis et al. |
| 6,353,763 B1 | 3/2002 | George et al. |
| 6,360,116 B1 | 3/2002 | Jackson et al. |
| 6,381,497 B1 | 4/2002 | Knowlton |
| 6,405,090 B1 | 6/2002 | Knowlton |
| 6,406,157 B1 | 6/2002 | Audet |
| 6,413,255 B1 | 7/2002 | Stern |
| 6,413,268 B1 | 7/2002 | Hartman |
| 6,416,514 B1 | 7/2002 | Ein-Gal |
| 6,419,674 B1 | 7/2002 | Bowser et al. |
| 6,425,912 B1 | 7/2002 | Knowlton |
| 6,430,446 B1 | 8/2002 | Knowlton |
| 6,433,343 B1 | 8/2002 | Cimino et al. |
| 6,436,051 B1 | 8/2002 | Morris et al. |
| 6,438,424 B1 | 8/2002 | Knowlton |
| 6,440,121 B1 | 8/2002 | Weber et al. |
| 6,452,912 B1 | 9/2002 | Leem |
| 6,453,202 B1 | 9/2002 | Knowlton |
| 6,461,354 B1 | 10/2002 | Olsen et al. |
| 6,461,378 B1 | 10/2002 | Knowlton |
| 6,461,567 B1 | 10/2002 | Hearst et al. |
| 6,462,070 B1 | 10/2002 | Hasan et al. |
| 6,470,216 B1 | 10/2002 | Knowlton |
| 6,471,716 B1 | 10/2002 | Pecukonis |
| 6,482,201 B1 | 11/2002 | Olsen et al. |
| 6,482,204 B1 | 11/2002 | Lax et al. |
| 6,487,447 B1 | 11/2002 | Weimann et al. |
| 6,493,940 B2 | 12/2002 | Westerhof et al. |
| 6,494,900 B1 | 12/2002 | Salansky et al. |
| 6,497,702 B1 | 12/2002 | Bernaz |
| 6,508,813 B1 | 1/2003 | Altshuler |
| 6,511,475 B1 | 1/2003 | Altshuler et al. |
| 6,514,243 B1 | 2/2003 | Eckhouse et al. |
| 6,514,248 B1 | 2/2003 | Eggers et al. |
| 6,517,532 B1 | 2/2003 | Altshuler et al. |
| 6,533,775 B1 | 3/2003 | Rizoiu et al. |
| 6,544,259 B1 | 4/2003 | Tsaliovich |
| 6,544,261 B2 | 4/2003 | Ellsberry et al. |
| 6,558,653 B2 | 5/2003 | Andersen et al. |
| 6,572,637 B1 | 6/2003 | Yamazaki et al. |
| 6,582,429 B2 | 6/2003 | Krishnan et al. |
| 6,594,905 B2 | 7/2003 | Furst et al. |
| 6,595,990 B1 | 7/2003 | Weinstein et al. |
| 6,597,946 B2 | 7/2003 | Avrahami |
| 6,602,245 B1 | 8/2003 | Thiberg |
| 6,611,706 B2 | 8/2003 | Avrahami et al. |
| 6,612,819 B1 | 9/2003 | Furst et al. |
| 6,618,620 B1 | 9/2003 | Freundlich et al. |
| 6,620,158 B2 | 9/2003 | Ronci |
| 6,629,974 B2 | 10/2003 | Penny et al. |
| 6,632,002 B1 | 10/2003 | Chubb et al. |
| 6,632,220 B1 | 10/2003 | Eggers et al. |
| 6,637,877 B1 | 10/2003 | Hartley et al. |
| 6,662,054 B2 | 12/2003 | Kreindel et al. |
| 6,663,620 B2 | 12/2003 | Altshuler et al. |

(56) References Cited

U.S. PATENT DOCUMENTS

| | | | |
|---|---|---|---|
| 6,676,655 B2 | 1/2004 | McDaniel | |
| 6,702,808 B1 | 3/2004 | Kreindel | |
| 6,708,060 B1 | 3/2004 | Avrahami et al. | |
| 6,711,435 B2 | 3/2004 | Avrahami | |
| 6,719,754 B2 | 4/2004 | Underwood et al. | |
| 6,723,092 B2* | 4/2004 | Brown et al. | 606/41 |
| D490,156 S | 5/2004 | Fischer et al. | |
| D490,526 S | 5/2004 | Jonsen | |
| 6,740,079 B1 | 5/2004 | Eggers et al. | |
| 6,743,211 B1 | 6/2004 | Prausnitz et al. | |
| 6,749,626 B1 | 6/2004 | Bhat et al. | |
| 6,758,845 B1 | 7/2004 | Weckwerth et al. | |
| 6,761,729 B2 | 7/2004 | Babaev | |
| 6,770,069 B1 | 8/2004 | Hobart et al. | |
| 6,773,431 B2 | 8/2004 | Eggers et al. | |
| 6,780,838 B2 | 8/2004 | Lipton et al. | |
| 6,795,728 B2 | 9/2004 | Chornenky et al. | |
| RE38,643 E | 11/2004 | Sugaya et al. | |
| 6,887,260 B1 | 5/2005 | McDaniel | |
| 6,889,090 B2 | 5/2005 | Kreindel | |
| 6,905,496 B1 | 6/2005 | Ellman et al. | |
| 6,918,907 B2 | 7/2005 | Kelly et al. | |
| 6,974,450 B2 | 12/2005 | Weber et al. | |
| 6,997,923 B2 | 2/2006 | Anderson et al. | |
| 7,006,874 B2 | 2/2006 | Knowlton et al. | |
| 7,013,179 B2* | 3/2006 | Carter et al. | 607/69 |
| 7,022,121 B2 | 4/2006 | Stern et al. | |
| 7,077,840 B2 | 7/2006 | Altshuler et al. | |
| 7,115,123 B2 | 10/2006 | Knowlton et al. | |
| 7,115,124 B1 | 10/2006 | Xiao | |
| 7,118,563 B2 | 10/2006 | Weckwerth et al. | |
| 7,141,049 B2 | 11/2006 | Stern et al. | |
| 7,153,298 B1 | 12/2006 | Cohen | |
| 7,204,832 B2 | 4/2007 | Altshuler et al. | |
| 7,234,239 B2 | 6/2007 | Saito et al. | |
| 7,238,183 B2 | 7/2007 | Kreindel | |
| 7,266,414 B2* | 9/2007 | Cornelius et al. | 607/122 |
| 7,275,819 B2 | 10/2007 | Bleau | |
| 7,278,991 B2 | 10/2007 | Morris et al. | |
| 7,278,993 B2 | 10/2007 | Kelly et al. | |
| 7,416,550 B2 | 8/2008 | Protsenko et al. | |
| 7,435,247 B2 | 10/2008 | Woloszko et al. | |
| 7,494,488 B2 | 2/2009 | Weber | |
| 7,517,344 B2 | 4/2009 | Van Hal et al. | |
| 7,601,149 B2 | 10/2009 | DiCarlo et al. | |
| 7,713,266 B2 | 5/2010 | Elkins et al. | |
| 7,771,419 B2 | 8/2010 | Carmel et al. | |
| 7,824,394 B2 | 11/2010 | Manstein | |
| 7,935,107 B2 | 5/2011 | Altshuler et al. | |
| 7,963,985 B2 | 6/2011 | Minamoto et al. | |
| 8,021,360 B2 | 9/2011 | Dunning et al. | |
| 8,034,052 B2 | 10/2011 | Podhajsky | |
| 8,109,927 B2 | 2/2012 | Kelly et al. | |
| 8,128,622 B2 | 3/2012 | Podhajsky et al. | |
| 8,133,216 B2 | 3/2012 | Knopp et al. | |
| 8,135,475 B2 | 3/2012 | Kreindel et al. | |
| 8,157,807 B2 | 4/2012 | Ferren et al. | |
| 8,202,268 B1 | 6/2012 | Wells et al. | |
| 8,206,381 B2 | 6/2012 | Lischinsky et al. | |
| 8,235,989 B2 | 8/2012 | Palanker et al. | |
| 8,292,882 B2 | 10/2012 | Danek et al. | |
| 8,506,564 B2* | 8/2013 | Long et al. | 606/41 |
| 2001/0007068 A1 | 7/2001 | Ota et al. | |
| 2002/0035363 A1 | 3/2002 | Edwards et al. | |
| 2002/0058936 A1 | 5/2002 | Avrahami et al. | |
| 2002/0104543 A1 | 8/2002 | Hollander et al. | |
| 2002/0120256 A1 | 8/2002 | Furuno et al. | |
| 2002/0120260 A1 | 8/2002 | Morris et al. | |
| 2002/0120261 A1* | 8/2002 | Morris et al. | 606/41 |
| 2002/0128641 A1* | 9/2002 | Underwood et al. | 606/32 |
| 2002/0128648 A1 | 9/2002 | Weber et al. | |
| 2002/0143373 A1 | 10/2002 | Courtnage et al. | |
| 2002/0147384 A1 | 10/2002 | Uchikubo | |
| 2002/0173780 A1 | 11/2002 | Altshuler et al. | |
| 2002/0183245 A1 | 12/2002 | Hasan et al. | |
| 2002/0190337 A1 | 12/2002 | House et al. | |
| 2002/0198575 A1 | 12/2002 | Sullivan | |
| 2003/0000449 A1 | 1/2003 | McDaniel et al. | |
| 2003/0032900 A1 | 2/2003 | Ella | |
| 2003/0032950 A1 | 2/2003 | Altshuler et al. | |
| 2003/0055413 A1 | 3/2003 | Altshuler et al. | |
| 2003/0055414 A1 | 3/2003 | Altshuler et al. | |
| 2003/0097162 A1 | 5/2003 | Kreindel | |
| 2003/0109871 A1 | 6/2003 | Johnson et al. | |
| 2003/0135250 A1 | 7/2003 | Lauman et al. | |
| 2003/0139790 A1 | 7/2003 | Ingle et al. | |
| 2003/0195494 A1 | 10/2003 | Altshuler et al. | |
| 2003/0199863 A1 | 10/2003 | Swanson et al. | |
| 2003/0199946 A1 | 10/2003 | Gutwein | |
| 2003/0216719 A1 | 11/2003 | Debenedictis et al. | |
| 2004/0010250 A1 | 1/2004 | Manna et al. | |
| 2004/0010298 A1 | 1/2004 | Altshuler et al. | |
| 2004/0015161 A1 | 1/2004 | Lovewell | |
| 2004/0015162 A1 | 1/2004 | McGaffigan | |
| 2004/0064167 A1 | 4/2004 | Berry et al. | |
| 2004/0133251 A1 | 7/2004 | Altshuler et al. | |
| 2004/0143308 A1 | 7/2004 | Lundahl et al. | |
| 2004/0147984 A1 | 7/2004 | Altshuler et al. | |
| 2004/0167501 A1 | 8/2004 | Island et al. | |
| 2004/0181216 A1 | 9/2004 | Kelly et al. | |
| 2004/0186466 A1 | 9/2004 | Chornenky | |
| 2004/0193234 A1 | 9/2004 | Butler | |
| 2004/0210214 A1* | 10/2004 | Knowlton | 606/41 |
| 2004/0236320 A1* | 11/2004 | Protsenko et al. | 606/32 |
| 2004/0260210 A1 | 12/2004 | Ella et al. | |
| 2004/0267252 A1 | 12/2004 | Washington et al. | |
| 2005/0015042 A1 | 1/2005 | Sun et al. | |
| 2005/0033286 A1 | 2/2005 | Eggers et al. | |
| 2005/0043653 A1 | 2/2005 | Trimmer et al. | |
| 2005/0049543 A1 | 3/2005 | Anderson et al. | |
| 2005/0075573 A1 | 4/2005 | Park et al. | |
| 2005/0085804 A1 | 4/2005 | McGaffigan | |
| 2005/0096646 A1 | 5/2005 | Wellman et al. | |
| 2005/0137654 A1 | 6/2005 | Hoenig et al. | |
| 2005/0137655 A1 | 6/2005 | MacFarland et al. | |
| 2005/0143793 A1 | 6/2005 | Korman et al. | |
| 2005/0147137 A1 | 7/2005 | Slatkine | |
| 2005/0149012 A1 | 7/2005 | Penny et al. | |
| 2005/0177139 A1 | 8/2005 | Yamazaki et al. | |
| 2005/0288680 A1 | 12/2005 | Ingle et al. | |
| 2006/0036300 A1 | 2/2006 | Kreindel | |
| 2006/0095096 A1 | 5/2006 | DeBenedictis et al. | |
| 2006/0149343 A1 | 7/2006 | Altshuler et al. | |
| 2006/0184024 A1 | 8/2006 | Da Silva et al. | |
| 2006/0200213 A1 | 9/2006 | McDaniel | |
| 2006/0206173 A1 | 9/2006 | Gertner et al. | |
| 2006/0224217 A1 | 10/2006 | Burgmann et al. | |
| 2006/0231568 A1 | 10/2006 | Lynn et al. | |
| 2006/0247741 A1 | 11/2006 | Hsu et al. | |
| 2006/0253112 A1 | 11/2006 | Suarez et al. | |
| 2006/0259102 A1 | 11/2006 | Slatkine | |
| 2006/0271028 A1 | 11/2006 | Altshuler et al. | |
| 2007/0016117 A1 | 1/2007 | Sliwa et al. | |
| 2007/0038206 A1 | 2/2007 | Altshuler et al. | |
| 2007/0093798 A1 | 4/2007 | DeBenedictis et al. | |
| 2007/0106349 A1 | 5/2007 | Karni et al. | |
| 2007/0129711 A1 | 6/2007 | Altshuler et al. | |
| 2007/0142881 A1 | 6/2007 | Hennings | |
| 2007/0191821 A1 | 8/2007 | Boxer Wachler | |
| 2007/0191827 A1 | 8/2007 | Lischinsky et al. | |
| 2007/0197895 A1 | 8/2007 | Nycz et al. | |
| 2007/0198004 A1 | 8/2007 | Altshuler et al. | |
| 2007/0206275 A1 | 9/2007 | Hemmer et al. | |
| 2007/0213696 A1 | 9/2007 | Altshuler et al. | |
| 2007/0239142 A1 | 10/2007 | Altshuler et al. | |
| 2007/0239143 A1 | 10/2007 | Altshuler et al. | |
| 2007/0239152 A1 | 10/2007 | Trezon | |
| 2007/0271714 A1 | 11/2007 | Adam et al. | |
| 2008/0051680 A1 | 2/2008 | Luebcke | |
| 2008/0071334 A1 | 3/2008 | Hoenig et al. | |
| 2008/0082090 A1 | 4/2008 | Manstein | |
| 2008/0123238 A1 | 5/2008 | Campos et al. | |
| 2008/0125658 A1 | 5/2008 | Lee et al. | |
| 2008/0139901 A1 | 6/2008 | Altshuler et al. | |

(56) References Cited

U.S. PATENT DOCUMENTS

| | | |
|---|---|---|
| 2008/0154247 A1 | 6/2008 | Dallarosa et al. |
| 2008/0183167 A1 | 7/2008 | Britva et al. |
| 2008/0188846 A1 | 8/2008 | Palanker et al. |
| 2008/0200910 A1 | 8/2008 | Burger et al. |
| 2008/0215124 A1 | 9/2008 | Wagenaar et al. |
| 2008/0221504 A1 | 9/2008 | Aghion |
| 2008/0294153 A1 | 11/2008 | Allshuler et al. |
| 2008/0306476 A1 | 12/2008 | Hennings et al. |
| 2009/0036953 A1 | 2/2009 | Gustavsson |
| 2009/0043293 A1 | 2/2009 | Pankratov et al. |
| 2009/0105706 A1 | 4/2009 | Livneh |
| 2009/0112205 A1 | 4/2009 | McGill et al. |
| 2009/0119834 A1 | 5/2009 | Kneale et al. |
| 2009/0171341 A1 | 7/2009 | Pope et al. |
| 2009/0182315 A1 | 7/2009 | Zigan et al. |
| 2009/0192503 A1 | 7/2009 | Epshtein et al. |
| 2009/0222023 A1 | 9/2009 | Boone et al. |
| 2009/0234341 A1 | 9/2009 | Roth |
| 2009/0234342 A1 | 9/2009 | Ely et al. |
| 2009/0240310 A1 | 9/2009 | Kennedy |
| 2009/0299361 A1 | 12/2009 | Flyash et al. |
| 2010/0010480 A1 | 1/2010 | Mehta et al. |
| 2010/0063565 A1 | 3/2010 | Beerwerth et al. |
| 2010/0145321 A1 | 6/2010 | Altshuler et al. |
| 2010/0185193 A1 | 7/2010 | Kreindel |
| 2010/0185194 A1 | 7/2010 | Kreindel |
| 2010/0198134 A1 | 8/2010 | Eckhouse |
| 2010/0211055 A1 | 8/2010 | Eckhouse et al. |
| 2010/0249772 A1 | 9/2010 | Mehta et al. |
| 2010/0274329 A1 | 10/2010 | Bradley et al. |
| 2011/0112405 A1 | 5/2011 | Barthe et al. |
| 2011/0137386 A1 | 6/2011 | Kreindel |
| 2011/0166559 A1 | 7/2011 | Eckhouse et al. |
| 2011/0196363 A1 | 8/2011 | Kreindel |
| 2012/0016354 A9 | 1/2012 | Epshtein et al. |
| 2012/0022512 A1 | 1/2012 | Vaynberg |
| 2012/0022518 A1 | 1/2012 | Levinson |
| 2012/0123397 A1 | 5/2012 | Epshtein et al. |
| 2012/0143178 A9 | 6/2012 | Mehta |
| 2012/0143270 A1 | 6/2012 | Mehta |
| 2012/0197242 A1 | 8/2012 | Rosenberg |
| 2012/0290023 A1 | 11/2012 | Boyden et al. |
| 2013/0144280 A1 | 6/2013 | Eckhouse et al. |
| 2013/0289679 A1 | 10/2013 | Eckhouse et al. |

FOREIGN PATENT DOCUMENTS

| | | |
|---|---|---|
| JP | 04299998 A2 | 10/1992 |
| JP | 06113920 A2 | 4/1994 |
| JP | 11132843 A2 | 12/1999 |
| JP | 2003034630 | 2/2003 |
| WO | WO-83/02389 A1 | 7/1983 |
| WO | WO-93/21992 A1 | 11/1993 |
| WO | WO-99/09143 A1 | 2/1999 |
| WO | WO-99/34867 A1 | 7/1999 |
| WO | WO-02/78644 A2 | 10/2002 |
| WO | WO-03/039367 A1 | 5/2003 |
| WO | WO-2006/128034 A1 | 11/2006 |
| WO | WO-02094116 A1 | 11/2013 |

\* cited by examiner

METHOD AND SYSTEM FOR INVASIVE SKIN TREATMENT

CROSS-REFERENCE TO RELATED APPLICATIONS

This application is being filed under 35 USC 111 and is a continuation of and claims the benefit of the filing date of U.S. patent application Ser. No. 10/931,271 that was filed on Sep. 1, 2004 now abandoned and bears the title of METHOD AND SYSTEM FOR INVASIVE SKIN TREATMENT.

FIELD OF THE INVENTION

The invention relates to methods and systems for skin treatment.

BACKGROUND OF THE INVENTION

Directed damage of the skin is used to stimulate regrowth of collagen and to improve skin appearance. A well known method of directed damage is ablating the epidermis using laser radiation having wavelengths strongly absorbed by water so as to heat the water to above boiling temperature. Typical lasers used for epidermis ablation are $CO_2$ and Er:YAG lasers. Ablating the epidermis using RF radiofrequency) current is described in U.S. Pat. No. 6,309,387. This treatment significantly reduces wrinkles and improves the skin appearance. The main disadvantages of skin resurfacing are the long healing period that can be over a month long and the high risk of dischromia. These disadvantages have reduced the popularity of ablative skin resurfacing in recent years.

Non-ablative skin resurfacing is based on heating of the dermis to a sub-necrotic temperature with simultaneous cooling of the skin surface. U.S. Pat. No. 5,810,801 describes penetrating the dermis with infrared laser radiation with dynamic cooling of the skin surface using a cryogen spray.

Wrinkles are created in skin due to the breakage of collagen fibers and to the penetration of fat into the dermal structure. Thus, destroying adipose cells and structure, can improve the surface structure. However, most wrinkle treatment methods target the collagen and do not have a significant effect on deep wrinkles. Radio frequency (RF) energy has been used for the treatment of the epidermal and dermal layers of the skin. For example, U.S. Pat. No. 6,749,626 describes use of RF for collagen formation in dermis. This patent describes a method for collagen scar formation. U.S. Pat. Nos. 6,470,216, 6,438,424, 6,430,446, and 6,461,378 disclose methods and apparatuses for affecting the collagen matrix using RF with special electrode structures together with cooling and smoothing of the skin surface. U.S. Pat. Nos. 6,453,202, 6,405,090, 6,381,497, 6,311,090, 5,871,524, and 6,452,912 describe methods and apparatuses for delivering RF energy to the skin using a membrane structure. U.S. Pat. Nos. 6,453,202 and 6,425,912 describe methods and apparatuses for delivering RF energy and creating a reverse temperature gradient on the skin surface. Although a non-ablative treatment is much safer and does not scar the skin tissue, the results of non-ablative treatments are less satisfactory.

A method described in US Patent Application No. 20030216719 attempts to maintain the efficiency of ablative treatment with a shorter healing time and a lower risk of adverse effects. The device described in that patent coagulates discrete regions of the skin where the regions have a diameter of tens of micrometers and the distance between the regions is larger than the regions themselves. This treatment provides skin healing within a few days but the results are very superficial and less spectacular than with $CO_2$ laser treatment, even after multiple treatments.

U.S. Pat. No. 6,277,116 describes a method of applying electromagnetic energy to the skin through an array of electrodes and delivery electrolyte using a microporous pad.

A device for ablation of the skin stratum corneum using RF electrodes is described in U.S. Pat. Nos. 6,711,435, 6,708,060, 6,611,706, and 6,597,946. However, the parameters of this device are optimized for the ablation of the stratum corneum so as to enhance drug penetration into the skin, and not for thermal collagen remodeling.

SUMMARY OF THE INVENTION

The present invention provides a system and method for simultaneously heating skin at a plurality of discrete regions of the skin. The invention may be used for collagen remodeling. In accordance with the invention RF energy is applied to the skin at a plurality of discrete locations on the skin. The RF energy is applied using an electrode having a plurality of spaced apart protruding conducting pins. When the electrode is applied to the skin surface, each protruding conducting pin contacts the skin surface at a different location, so that the plurality of pins contacts the skin at a plurality of discrete locations. An RF voltage is then applied to the electrode so as to generate an electric current in the skin that heats the skin to a coagulation temperature simultaneously at a plurality of discrete regions of the skin. Coagulation temperatures are typically in the range of about 60° C. to about 70° C.

The protruding pins may have blunt tips which do not penetrate into the skin when the electrode is applied to the skin. In this case, the discrete regions of treated skin are located at the skin surface in the epidermis. Alternatively, the pins may have sharp tips that allow the protruding pin to penetrate the skin into the dermis. In this way, the discrete regions of treated skin are located in the dermis.

In another embodiment, the protruding elements are provided with sharp tips that allow the elements to penetrate into the skin. After application of the RF current in the skin, the protruding elements are pressed into the skin and an electrical current is then generated that coagulates tissue in the vicinity of the tip of each protruding element. The mechanical properties of the skin are changed after coagulation and the protruding elements may penetrate inside the skin without excessive pressure. A pre-pulse of RF energy can be applied to the skin in order to soften the skin tissue so as to facilitate penetration of the protruding elements into the skin.

The surface of the skin may be pre-cooled and/or cooled during the treatment to avoid damage to the skin in the area between protruding elements. Skin cooling may be provided by contact cooling or by applying a pre-cooled liquid or cryogen spray.

The invention may be used in wrinkle treatment, collagen remodeling, skin tightening, loose skin treatment, sub-cutaneous fat treatment or skin resurfacing.

Thus in its first aspect, the invention provides a system for simultaneously heating a plurality of discrete skin volumes to a coagulation temperature, comprising:
  (a) an applicator comprising an electrode having a plurality of spaced apart protruding conducting elements configured to contact the skin surface at a plurality of discrete locations; and
  (b) a controller configured to apply a voltage to the electrode so as to simultaneously heat a plurality of skin volumes to a coagulation temperature when the applicator is applied to the skin surface.

In its second aspect, the invention provides a method for simultaneously heating a plurality of discrete skin volumes to a coagulation temperature, comprising:

(a) applying an applicator to the skin surface, the applicator comprising an electrode having a plurality of spaced apart protruding conducting elements configured to contact the skin surface at a plurality of discrete locations; and (b) applying a voltage to the electrode so as to simultaneously heat a plurality of skin volumes to a coagulation temperature.

In the case when protruding part of the electrode penetrates within the skin the size of protruding elements should be small enough to avoid significant damage of the skin surface. Preferable size of protruding elements is from 10 to 200 microns and coagulation depth can be varied from 100 microns up to 2 mm for invasive electrodes.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF PREFERRED EMBODIMENTS

Figure 1:
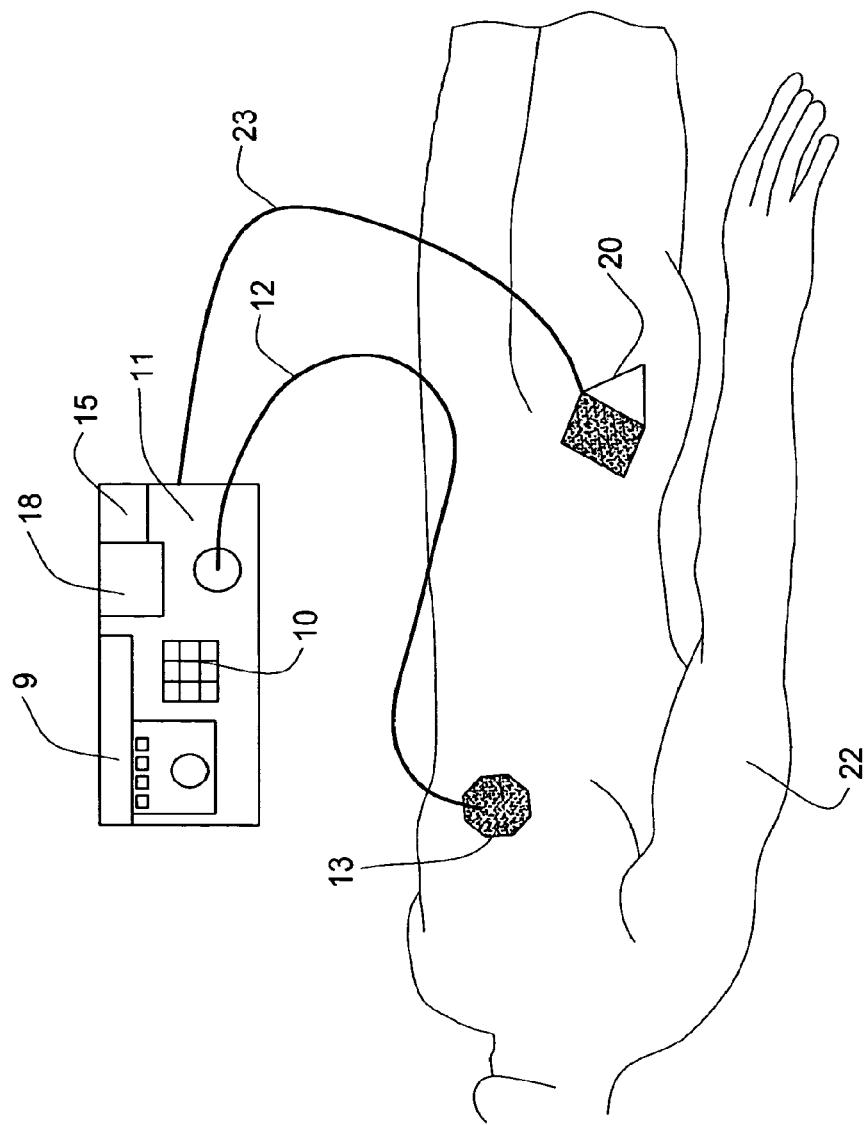
FIG. 1 shows a system for treating skin simultaneously at a plurality of discrete regions of skin, in accordance with the invention.

FIG. 1 shows a system for applying RF energy to a plurality of discrete regions of skin in accordance with the invention. The system includes an applicator 13, to be described in detail below, configured to apply RF energy simultaneously to a plurality of discrete regions of skin of an individual 22. The applicator 13 is connected to a control unit 11 via a cable 12. The control unit 11 includes a power source 18. The power source 18 is connected to an RF generator 15 that is connected to electrodes in the applicator 13 via wires in the cable 12. The control unit 11 has an input device such as a keypad 10 that allows an operator to input selected values of parameters of the treatment, such as the frequency, pulse duration and intensity of the RF energy. The control unit 11 optionally contains a processor 9 for monitoring and controlling various functions of the device.

Figure 2:
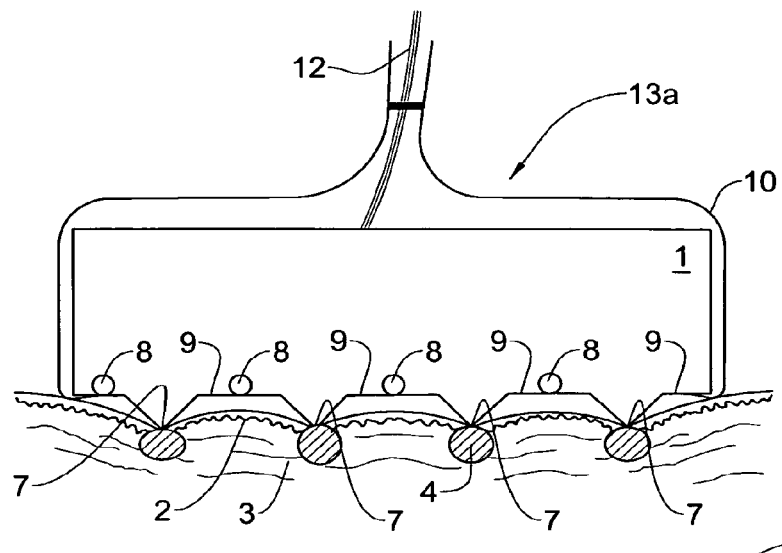
FIG. 2 shows an applicator for use in the system of FIG. 1.

FIG. 2 shows an applicator 13a that may be used for the applicator 13 in accordance with one embodiment of the invention. The applicator 13a comprises an electrode 1 from which a plurality of protruding conducting elements 5 extend. Each protruding element 5 (referred to herein as a "pin") terminates in a tip 7 having a high curvature. The electrical current from the tips is much higher than from flat parts 6 of the electrode. Skin volumes 4 around the tips 7 are therefore heated to a much higher temperature than the surrounding dermis 3 and epidermis 2, so that the skin volumes 4 may be heated to a coagulation temperature, while the skin temperature in the outside the volumes 4 are not heated to a coagulation temperature. The electrical energy is adjusted to selectively damage skin adjacent to tips so that the treatment of the skin occurs simultaneously at a plurality of discrete volumes 4. The pulse duration is preferably short enough to prevent significant heat diffusion far from the tips. In order to limit significant heat transfer from the tips, the pulse duration should preferably not exceed 200 ms. The selectivity of the treatment can be improved by electrode cooling of the skin surface. Cooling also causes a more uniform heat distribution at the tips. This can be achieved by circulating a cooling fluid through tubes 8 in the flat regions 9 between the pins 5. The electrode 1 is contained in a housing 10 connected to the cable 12. A wire 13 extending through the cable 12 electrically connects the electrode 1 with a terminal of the power source 18. A second terminal of the power supply 18 may be connected to a ground electrode 20 via a cable 23 (See FIG. 1).

Figure 3:
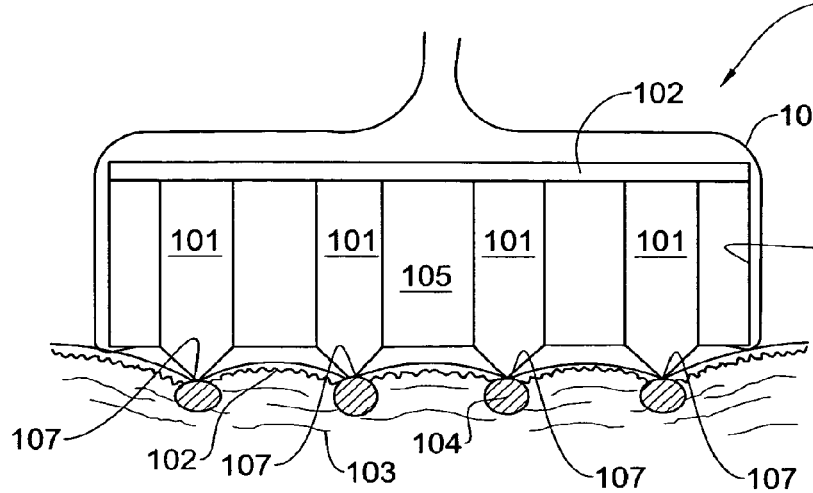
FIG. 3 shows a second applicator for use in the system of FIG. 1.

FIG. 3 shows an applicator 13b that may be used for the applicator 13 in accordance with another embodiment of the invention. The applicator 13b comprises an electrode 100 consisting of a plurality of conducting pins 101 extending from a conducting plate 102. The pins 101 are separated by electrical insulating material 105. The applicator 13b is used similarly as the applicator 13a to deliver electrical current to discrete volumes of skin 4.

The pins 5 in the applicator 13a and the pins 101 in the applicator 13b are provided with blunt tips 7 and 107, respectively. This prevents the pins 5 and 101 from penetrating into the skin when the electrode 13a or 13b is applied t the skin surface. Thus, the applicators 13a and 13b provide simultaneous non-invasive coagulation of skin regions 4.

Figure 4:
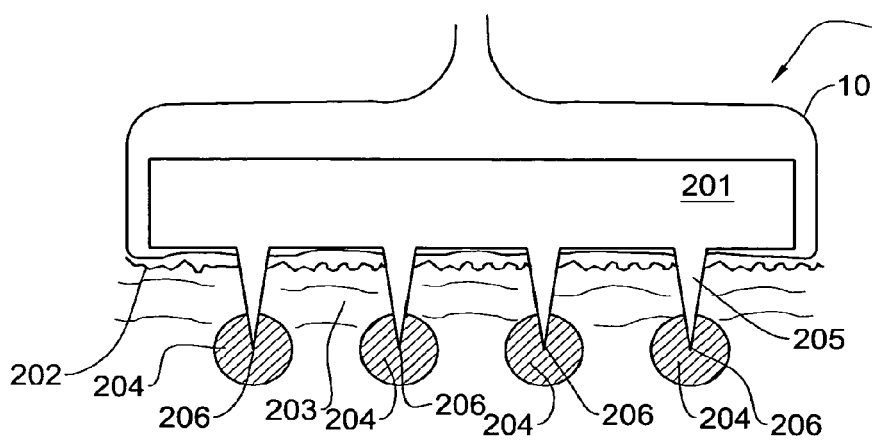
FIG. 4 shows a third applicator for use in the system of FIG. 1.

FIG. 4 shows an applicator 13c that may be used for the applicator 13 in accordance with another embodiment of the invention. The applicator 13c is configured to be used for invasive collagen remodeling. The applicator 13c includes an electrode 201 having a plurality of protruding conducting pins 205. The pins 205 have sharp tips 206 that are configured to penetrate through the epidermis 202 into the dermis 203 when pressed on the skin as shown in FIG. 4. The applicator 13c is used similarly to the applicators 13a and 13b so that the treatment of the skin occurs simultaneously in a plurality of discrete skin volumes 204. However, unlike the discrete volumes 4, which are located in the epidermis (see FIGS. 2 and 3), the volumes 204 are located below the surface in the dermis 203 (FIG. 4). This reduces skin redness that sometimes occurs when the treated regions are in the epidermis. A maximal current density is created at the tips of the pins 205. The sides of the protruding elements may be coated with insulating material to avoid skin heating around the pins 205 (not shown).

The present invention can be combined with other methods of skin treatment including laser treatment. For example non-ablative collagen remodeling by laser radiation may be combined with the invasive RF heating of the skin dermis in accordance with the invention.

The preferable parameters for non-invasive skin coagulation in accordance with the invention are as follows:

Electrode size above 0.3 cm;
Protruding element at contact with the skin up to 0.5 mm
Protruding element height about 1 mm.
Distance between protruding elements at least twice the element diameter;
Current density: over 1 A/cm$^2$;
RF current pulse duration: not longer than 0.5 sec;
The optimal parameters for invasive skin coagulation:
Electrode size above 0.3 cm;
Pin diameter at contact with the skin not larger than 0.3 mm
Pin protruding height above 1 mm.
Distance between pins at least 1 mm;
Current density above 0.1 A/cm$^2$;
RF current pulse duration not longer than 0.5 sec;

The invention claimed is:

1. A system for applying RF energy to a plurality of discrete regions of skin, said system comprising:
   an applicator comprising an electrode including flat parts and a plurality of protruding electrically conducting spaced apart pins terminated by sharp tips, the pins configured to penetrate throguh epidermis into the dermis and apply RF energy to one or more discrete tissue volumes that are completely located in the dermis, so as to heat the tissue volumes to a coagulation temperature;
   a radio frequency energy source configured to apply radio frequency energy to the electrode with at least the plurality of protruding electrically conducting spaced apart pins to generate an electrical current in the dermis from the tips higher than from the flat parts of the electrode;
   a control unit configured to allow input selected values of parameters of the RF energy to at least one located below skin tissue surface dermal tissue volume producing dermal tissue temperature increase to cause thermal collagen remodeling; and
   tubes in flat regions between the protruding electrically conducting spaced apart pins for circulating a cooling fluid there through and cooling the electrode and the skin surface.

2. The system according to claim 1, wherein the selected values of parameters are at least one of a group consisting of frequency, pulse duration and intensity of the RF energy.

3. The system according to claim 2, wherein the radio frequency energy source is a voltage source configured to apply voltage pulses with pulse duration shorter than 200 ms to the conductive pins.

4. The system according to claim 1 wherein in order to avoid skin redness the sides of the pins are coated with insulating material.

5. The system according to claim 1 wherein the current conducting pins are spaced apart by a distance of at least 1 mm.

6. A method for heating a plurality of discrete dermis volumes to a coagulation temperature, said method comprising:
   applying to skin surface an applicator comprising at least one electrode including flat parts and a plurality of protruding electrically conducting spaced apart pins terminated by sharp tips, the tips configured to penetrate through epidermis into dermis reaching a plurality of discrete volumes located in dermis;
   applying a voltage to the at least one electrode with the plurality of protruding electrically conducting spaced apart pins to generate in the dermis an electrical current from the tips higher than from the flat parts of the electrode simultaneously heating a plurality of dermis volumes to a coagulation temperature; and
   cooling the electrode and the skin surface by circulating a cooling fluid through tubes in the flat parts between the protruding electrically conducting spaced apart pins.

7. The method according to claim 1, further comprising adjusting RF energy to selectively damage dermis volumes adjacent to the pins terminated by tips with high curvatures so that treatment of the dermis occurs simultaneously at a plurality of discrete dermis volumes.

8. The method according to claim 7, wherein the selectively damaged dermal volumes located underneath skin surface are separated by not damaged volumes of dermal tissue.

9. The method according to claim 1, wherein said volumes are completely located within the dermis below the skin surface.

10. The method according to claim 1, wherein the volumes located below skin tissue surface do not include an epidermal tissue volume.

11. The method according to claim 1, further comprising avoiding skin heating and redness around the pins by coating the sides of the pins with insulating material.

12. A method for invasive collagen remodeling with reduced skin redness, the method comprising:
   applying to the skin an electrode including flat parts and a plurality of spaced apart protruding conducting pins terminated by sharp tips;
   pressing the electrode such that protruding conducting pins terminated by sharp tips penetrate into the dermis;
   supplying RF voltage to the electrode and treating the skin simultaneously in a plurality of discrete skin volumes located in the dermis;
   cooling the electrode and the skin surface by circulating a cooling fluid through tubes in the flat parts between the protruding electrically conducting spaced apart pins; and
   wherein location of the plurality of discrete skin volumes located in the dermis reduces skin redness occurring at the treated regions of the skin.

* * * * *